(12) United States Patent
Truax

(10) Patent No.: US 7,749,191 B2
(45) Date of Patent: Jul. 6, 2010

(54) DEVICE AND METHOD FOR DRUG DELIVERY

(75) Inventor: Pamela Truax, Gurnee, IL (US)

(73) Assignee: Beutlich LP, Pharmaceuticals, Waukegan, IL (US)

( * ) Notice: Subject to any disclaimer, the term of this patent is extended or adjusted under 35 U.S.C. 154(b) by 29 days.

(21) Appl. No.: 12/052,402

(22) Filed: Mar. 20, 2008

(65) Prior Publication Data

US 2009/0240196 A1 Sep. 24, 2009

(51) Int. Cl.
*A61M 37/00* (2006.01)

(52) U.S. Cl. ..................................... 604/90; 604/85

(58) Field of Classification Search ............. 604/82–92, 604/232–234; 128/200.4
See application file for complete search history.

(56) References Cited

U.S. PATENT DOCUMENTS

| | | | |
|---|---|---|---|
| 3,552,387 A * | 1/1971 | Stevens ....................... | 604/88 |
| 3,797,492 A | 3/1974 | Place | |
| 4,265,760 A * | 5/1981 | Abel et al. ................... | 210/282 |
| 5,060,825 A | 10/1991 | Palmer et al. | |
| 5,122,117 A * | 6/1992 | Haber et al. .................. | 604/90 |
| 5,137,528 A * | 8/1992 | Crose .......................... | 604/415 |
| 5,199,604 A | 4/1993 | Palmer et al. | |
| 5,215,079 A | 6/1993 | Fine et al. | |
| 5,860,957 A | 1/1999 | Jacobsen et al. | |
| 6,045,534 A | 4/2000 | Jacobsen et al. | |
| 6,090,070 A | 7/2000 | Hager et al. | |
| 6,210,713 B1 * | 4/2001 | Wong et al. .................. | 424/473 |
| 6,398,774 B1 | 6/2002 | Penner et al. | |
| 6,569,123 B2 | 5/2003 | Alchas et al. | |
| 6,569,143 B2 | 5/2003 | Alchas et al. | |
| 6,689,118 B2 | 2/2004 | Alchas et al. | |
| 6,776,776 B2 | 8/2004 | Alchas et al. | |
| 7,195,623 B2 | 3/2007 | Burroughs et al. | |
| 7,204,822 B1 | 4/2007 | Penner et al. | |
| 7,225,805 B2 | 6/2007 | Bacon | |
| 7,255,684 B2 * | 8/2007 | Zubry ........................ | 604/131 |
| 2004/0249339 A1 * | 12/2004 | Willis et al. .................. | 604/70 |
| 2007/0051362 A1 | 3/2007 | Sullivan et al. | |
| 2007/0112310 A1 | 5/2007 | Lavi et al. | |
| 2008/0312587 A1 * | 12/2008 | Kugelmann et al. .......... | 604/84 |

OTHER PUBLICATIONS

Swab Plus OEM Advertisement, available prior to Mar. 20, 2008, 2 pages.
Beutlich Pharmaceuticals, Beutlich "What's New" Page, website <http://www.beutlich.com/news.htm> printed on Dec. 18, 2007, 3 pages.

* cited by examiner

*Primary Examiner*—Nicholas D Lucchesi
*Assistant Examiner*—Gerald Landry, II
(74) *Attorney, Agent, or Firm*—K&L Gates LLP

(57) ABSTRACT

Devices and methods of delivering a known quantity of a substance are provided. In particular, a substance delivery device is provided having a cartridge containing a known amount of the substance that is removably attachable to a pressure source such that substantially all of the amount of the substance is discharged from the cartridge upon actuation of the pressure source. The devices and methods provided are particularly applicable to the delivery of a drug or medicament.

7 Claims, 3 Drawing Sheets

DEVICE AND METHOD FOR DRUG DELIVERY

BACKGROUND

Drugs are often administered to patients from containers that include more than a single dose of the drug. Certain known drug delivery containers enable patient or provider control of or measurement of the dose of the drug delivered from such containers to allow delivery of less than all of the drug in the container at a particular time. For example, cough syrup is typically packaged and sold in a 4 fluid ounce bottle containing nearly 12 doses of 2 teaspoons each. To administer the cough syrup, the medicine is poured into a teaspoon or a cup having graduated markings along the sides of the cup to measure the amount of medicine that equals a teaspoon. Another example is a syringe which contains more volume of a drug than the volume of a single dose to be administered by a provider to the patient. For example, 10 ml of a drug may be provided in a 10 cc syringe when only 1 cc is to be administered to the patient. Graduated markings indicating volume within the syringe enables the provider to know how far to push the plunger of the syringe to deliver 1 cc of the drug to the patient. Another known example is an infusion pump. Infusion pumps are typically configured to pump a precisely measured aliquot of a drug from a larger volume of the drug typically provided in an IV bag. Each of these examples enable the health care provider to administer a defined amount or metered dose of the drug and to track, record and account for how much of the drug was delivered to the patient.

Other drug delivery mechanisms provide much more limited control of, and variability in, the amount of drug delivered from dose to dose. For example, drugs administered as aerosols or sprays are typically pressurized or pumped from a container containing multiple doses of the drug. Administration of a drug using these types of mechanisms can result in substantial variability between delivered doses and an inability to know for certain how much drug is delivered to a patient. For example, in aerosol or spray containers, air may replace the drug as a portion of the drug in the container is released or pumped from the container resulting in less than the desired amount or a different amount of the drug being delivered from dose to dose. Also, a provider may actuate or depress the release mechanism a different number of times or may not keep track of the number of times the release mechanism is actuated or depressed when delivering the drug to a patient or themselves. Furthermore, the provider may only partially actuate or depress the release mechanism or may actuate or depress the release mechanism to a different extent for each delivery of the drug. Such variability between doses and an inability to document how much of a drug is actually delivered to a patient may expose the patient to unnecessary risks such as overdose (and thus less efficiency), side effects, densensitization to the drug and the like. There is therefore a need for improved drug delivery devices.

SUMMARY

The present disclosure relates to devices and methods for delivering a predetermined amount of a substance such as a drug to a subject such as a patient. In particular, the present disclosure relates to a drug cartridge, and also to a drug delivery device including the drug cartridge, configured to deliver a predetermined dose of a drug to a patient.

In an embodiment of the present disclosure, the drug delivery device includes a predetermined amount of a drug contained within a drug cartridge. In an embodiment, the drug cartridge is in the form of a cylindrical tube defining a fluid passageway between a proximal end and a distal end of the drug cartridge. The drug cartridge is sized to contain the predetermined amount of the drug within the fluid passageway of the drug cartridge. The distal end of the drug cartridge includes an opening through which the predetermined amount of the drug can be discharged from the drug cartridge. [The proximal end of the drug cartridge is configured to be removably attached to a pressure source to form a fluid connection with the pressure source.]

In an embodiment, the drug cartridge includes walls or barriers adapted to protect the contents of the drug cartridge. In an embodiment, the barriers are adapted to be removed from the drug cartridge prior to discharging the predetermined amount of the drug from the drug cartridge. In an embodiment, the drug cartridge includes one or more closed end portions, each associated with one opening of the drug cartridge. Each closed end portion may be integral with the drug cartridge or configured as a cap that can cover the opening of at least one of the openings of the drug cartridge. In an embodiment, the closed end portion of the drug cartridge is configured to being punctured, removed, broken away from the drug cartridge at a weakened portion of the drug cartridge or any other suitable mechanism for opening the fluid passageway to enable release of the drug from the drug cartridge.

In an embodiment, the drug cartridge includes one or more pharmaceutically acceptable retention barriers positioned within the fluid passageway to prevent premature release of the drug from the drug cartridge until the drug is exposed to the pressurized fluid released from the pressure source. In one embodiment, the pharmaceutically acceptable retention barrier is positioned within the fluid passageway between the drug and the opening of the distal end of the drug cartridge and a pharmaceutically acceptable retention barrier is positioned within the fluid passageway between the drug and the opening of the proximal end of the drug cartridge. In other embodiments, pharmaceutically acceptable retention barriers separate two or more predetermined amounts of different drugs contained within a single drug cartridge When the proximal end of the drug cartridge is attached to the pressure source, the fluid connection between the drug cartridge and the pressure source channels the pressurized fluid released from the pressure source into the proximal end of the drug cartridge and through the fluid passageway of the drug cartridge toward the distal end of the drug cartridge. This directional flow of the pressurized fluid, in turn, forces the predetermined amount of the drug and any pharmaceutically acceptable barriers from the drug cartridge through its open distal end for delivery to a patient.

An embodiment of the present disclosure includes a method of delivering one or more of predetermined doses of a drug. The method includes providing a first drug cartridge containing a first predetermined amount of the drug. The first drug cartridge is configured to being removably attached to a pressure source to form a fluid connection between a fluid passageway of the drug cartridge and the pressure source. The method further includes exposing the contents of the drug cartridge to a pressure from the pressure source to discharge the first predetermined amount of the drug from the first drug cartridge. Once the first predetermined amount of the drug is discharged from the first drug cartridge, the first drug cartridge is removed from the pressure source, and a second drug cartridge containing a second predetermined dose of the drug is attached to the pressure source to form a fluid connection between the fluid passageway of the second drug cartridge and the pressure source. The pressure source is actuated to discharge the second predetermined dose of the drug from the second drug cartridge. In an embodiment, the pressure source is, configured to discharging the predetermined dose of the drug from multiple drug cartridges.

In an embodiment, the predetermined amount of drug in the first drug cartridge and the predetermined amount of drug in the second drug cartridge each constitute a single dose of the drug. In an embodiment, the drug in the first drug cartridge is different from the drug in the second drug cartridge. In an embodiment, the concentration of the drug in the first drug cartridge is different from the concentration of the drug in the second drug cartridge.

It is therefore an advantage of the embodiments of the present disclosure to provide a device for administering a precise amount of a substance such as a drug.

Another advantage of the present disclosure includes administering a precise dose of drugs that are typically administered in variable unknown amounts from a collection of multiple doses of the drug.

A further advantage is providing a known amount of a drug in discreet packaging containing information of the drug to enable a provider to record exactly what is administered to a patient for clinical purposes, billing purposes and other information tracking purposes.

Additional features and advantages are described herein, and will be apparent from, the following Detailed Description and the figures.

DETAILED DESCRIPTION

The present disclosure relates to substance delivery devices and methods of delivering a predetermined amount of a substance to a subject such as a patient. In particular, the present disclosure relates to a drug cartridge and a drug delivery device including the drug cartridge configured to deliver a predetermined dose of a drug to a patient.

Figure 1:
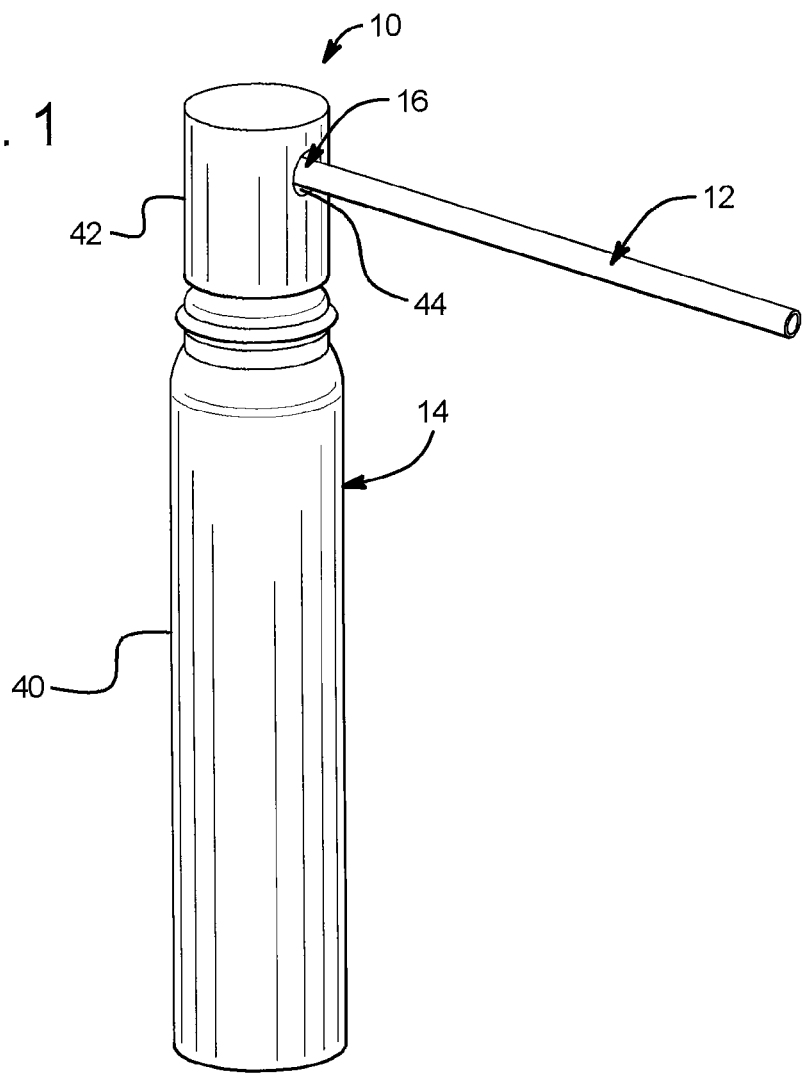
FIG. 1 is a perspective view of a drug delivery device according to an embodiment of the present disclosure.
Figure 2:
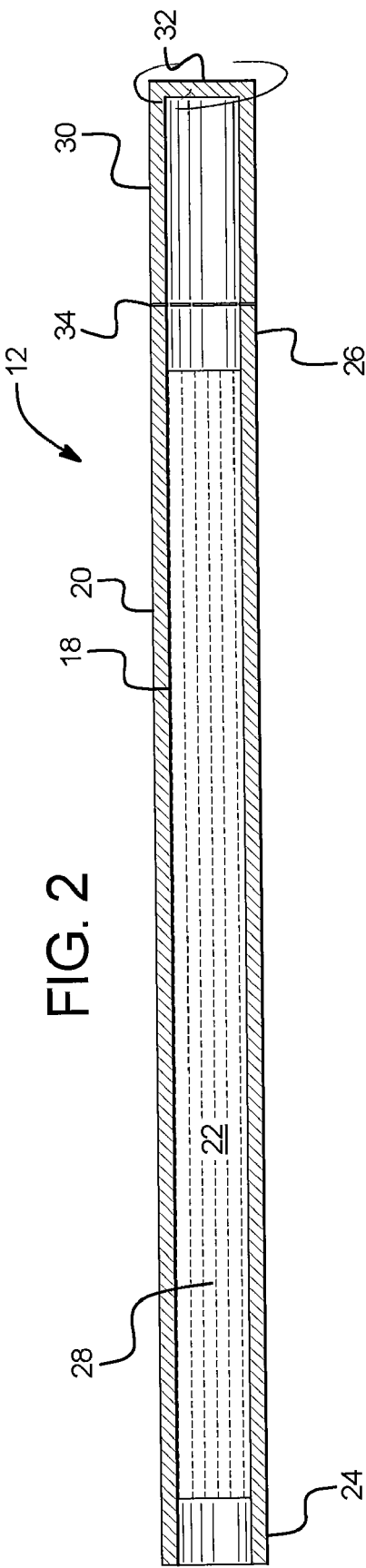
FIG. 2 is a cross-sectional view of a drug cartridge according to an embodiment of the present disclosure.

Referring to the Figures, and, in particular, to FIGS. 1 and 2, in an embodiment of the present disclosure, a drug delivery device 10 includes a drug cartridge 12 and a pressure source 14. The drug cartridge 12 is adapted to be removably connected to the pressure source 14 to form a fluid tight connection 16 between the drug cartridge 12 and pressure source 14.

In the illustrated embodiment, the drug cartridge 12 is in the form of a substantially hollow cylindrical tube having an inner wall 18 and an outer wall 20. The length of the drug cartridge 12 is greater than the diameter of the inner wall 18 of the drug cartridge 12. The inner wall 18 of the drug cartridge 12 defines a fluid passageway 22 through the drug cartridge 12 between a proximal end portion 24 and a distal end portion 26 of the drug cartridge 12. The drug cartridge 12 is sized to enclose or contain a predetermined amount of a drug or medicament 28 within the fluid passageway 22 of the drug cartridge 12 to be delivered to a patient or other subject. The diameter of the inner wall 18 of the drug cartridge 12 is sized to retain the drug 28 based on cohesive forces between the drug 28 and the inner wall 18 of the drug cartridge 12. In an embodiment, the drug cartridge 12 is translucent to enable a provider to determine if the drug 28 has been administered from the drug cartridge 12. It should be appreciated that the drug cartridge may be transparent, opaque partially, transparent or partially opaque.

The drug 28 may include any suitable agent, pharmaceutical or medicament that is able to be stored in and administered from the drug cartridge of the present disclosure. The drug 28 may include any type of drug, delivered to a patient through any route of administration including topical, oral, nasal, vaginal, rectal, sublingual, endotracheal, inhalation, and any other suitable route of administration. The drug 28 may be delivered in any suitable amount, and in any suitable formulation physical state such as a liquid, gel, gas, or certain solids, such as a powder form, or any phases therebetween and combinations thereof. It should be appreciated that drugs administered topically, drugs in liquid or semi-solid form, and drugs that are administered in relatively low volume are particularly suitable for delivery using the embodiments of the present disclosure.

The predetermined amount of the drug 28 includes an entire amount of a single or unit dose of the drug. Alternatively, the predetermined amount of the drug 28 includes a portion of a unit dose of the drug. In such an embodiment, the predetermined amount of the drug 28 contained in more than one drug cartridge 12 is delivered to a patient to administer a single unit dose of the drug to the patient. For example, the predetermined amount of the drug 28 contained within one drug cartridge 12 may be one-half of a single dose. Accordingly, the predetermined amount of the drug 28 of two drug cartridges 12 is delivered to a patient to administer a single dose of the drug to the patient.

The distal end portion 26 includes a removable closed end portion 30. The closed end portion 30 includes a wall 32 configured to block flow of a fluid from the fluid passageway 22. The closed end portion 30 of the drug cartridge 12 is separated from the remaining length of the drug cartridge 12 by a weakened portion 34. The weakened portion 34 enables a user to break off the closed end portion 30 to create an opening into the fluid passageway 22 of the drug cartridge 12 sufficient to allow discharge of the predetermined amount of the drug from the drug cartridge. It should be appreciated that a weakened portion of the drug cartridge 12 may be associated with the proximal end 24 of the drug cartridge 12 or both distal end 26 and proximal end 24 of the drug cartridge 12.

The pressure source 14 includes a container 40 configured to retaining a fluid at a pressure sufficient to create an expulsion pressure. As referred to herein, the expulsion pressure is the amount of pressure necessary to substantially expel the predetermined amount of the drug 28 from the drug cartridge 12. The container 40 is sized and configured to hold a volume of fluid sufficient to generate an expulsion pressure at least once, and, in an embodiment, the container 40 is sized and configured to hold a volume of fluid sufficient to generate an expulsion pressure for each dose of the drug 28. It should be appreciated that in various embodiments of the present disclosure, the container 40 is sized and configured to hold a volume of fluid sufficient to generate an expulsion pressure of multiple predetermined amounts of the drug 28.

The fluid in the container 40 includes a pharmaceutically acceptable gas, liquid or combination thereof that is compatible with the drug to be delivered. The gas may include any suitable gas that is configured to being pressurized within the container to generate an expulsion pressure upon its release from the container. In one embodiment, the fluid in the container 40 includes a nitrogen gas that is pharmaceutically acceptable and compatible with the drug 28 in the drug cartridge 12 such that contact of the drug 28 by the fluid does not substantially alter the properties of the drug 28. It should be appreciated that other pharmacologically acceptable and compatible gases or liquids may be used as fluids according to the embodiments of the present disclosure. Other suitable gases may include, but are not limited to, oxygen, carbon dioxide, butane, propane and combinations thereof. Suitable liquids may include, but are not limited to, water, normal saline, the carrier of the drug, and combinations thereof.

The fluid is stored within the container 40 at a pressure sufficient to create a pressure on the drug 28 in the drug cartridge 12 at least as great as the expulsion pressure. For example, in an embodiment, the fluid is pressurized within the container at a pressure of from about 40 psi to about 70 psi. It should be appreciated that the greater viscosity of the drug and the less the diameter of the drug cartridge, the greater the pressure required to reach the expulsion pressure. It should be further appreciated that increasing the pressure on the fluid stored within the container 40 enables the drug 28 to be released from the drug cartridge 12 at an increased rate.

The release mechanism 42 includes any suitable configuration enabling a controlled release of a sufficient amount of fluid to create a pressure on the drug 28 in the drug cartridge 12 at least as great as the expulsion pressure. In addition, the release mechanism 42 may be configured to control the speed of release of the drug 28 from the drug cartridge 12. In an embodiment, the release mechanism 42 may be activated by finger control to release the pressurized fluid. It should be appreciated that the release mechanism 42 may include any other suitable mechanism that enables a controlled release of pressurized fluid at an expulsion pressure. In an embodiment, a predetermined amount of the pressurized fluid is released upon actuation of the release mechanism 42 of the pressure source 14.

The proximal end portion 24 of the drug cartridge 12 is configured to removably attach to the pressure source 14 to form a fluid connection 16 with the pressure source 14. The pressure source 14 includes a port 44 that is configured to receive the proximal end 24 of the drug cartridge 12. In the illustrated embodiment, the port 44 includes a male connector (not illustrated). The male connector includes a lumen through which the pressurized fluid is configured to flowing from the pressure source 14. The male connector includes an outer wall diameter substantially equal to the inner wall 18 diameter at the proximal end 24 of the drug cartridge 12. The male connector of the port 44 is configured to be inserted into the fluid passageway 22 of the proximal end 24 of the drug cartridge 12. At least a portion of the inner wall 18 of the proximal end 24 of the drug cartridge 12 engages at least a portion of the outer wall of the port male connector to form a friction fit seal and to establish fluid communication between the lumen of the male connector and the fluid passageway 22 of the drug cartridge 12.

In an embodiment, the internal wall of the port 44 is shaped and sized substantially equal to the shape and size of the outer wall 20 of the proximal end 24 of the drug cartridge 12. At least a portion of the outer wall 20 of the drug cartridge 12 engages at least a portion of the inner wall of the port 44 to form a friction fit seal between the pressure source 14 and the drug cartridge 12. It should be appreciated that the drug delivery device may include other suitable mechanisms for connecting or attaching the drug cartridge to the pressure source such as a luer-lock connection, screw fit and the like. In such embodiments, either of the proximal end of the drug cartridge and the port of the pressure source are configured to act as the male or female portion of the connection.

Upon activation of the release mechanism 42 of the pressure source 14, the fluid connection 16 channels the pressurized fluid released from the pressure source 14 into the proximal end 24 of the drug cartridge 12 and through the fluid passageway 22 of the drug cartridge 12 toward the distal end 26 of the drug cartridge 12. The flow of the pressurized fluid from the pressure source 14 through the fluid passageway 22 of the drug cartridge 12 from its proximal end 24 to its distal end 26, in turn, forces the predetermined amount of the drug 28 from the drug cartridge 12 through its open distal end 26.

Figure 3:
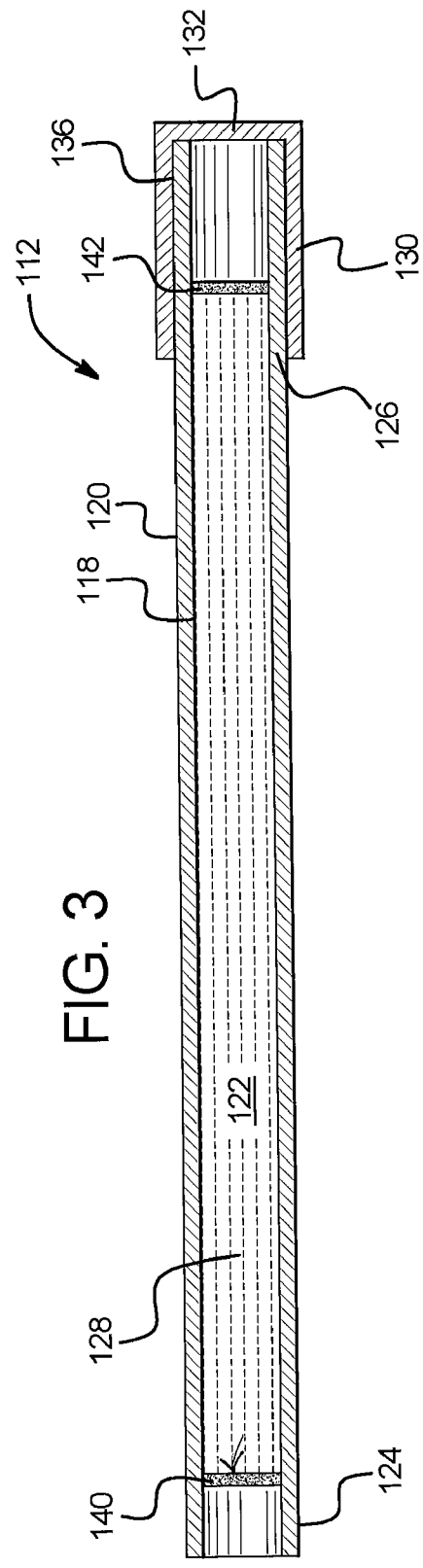
FIG. 3 is a cross-sectional view of a drug cartridge according to an embodiment of the present disclosure.

As illustrated in FIG. 3, in an alternative embodiment, the drug cartridge 120 includes a closed end portion 130 that is configured as a removable cap structure. The closed end portion 130 includes a substantially hollow tube having an inner diameter substantially equal to the outer diameter of the drug cartridge to enable the inner wall 136 of the closed end portion 130 to slidably engage the outer wall 120 of the open distal end portion 126 of the drug cartridge 112 to form a friction fit seal with the drug cartridge 112. The closed end portion 130 includes a wall 132 configured to block flow of a fluid from the fluid passageway 122. It should be appreciated that another closed end portion 130 may be associated with the proximal end 124 of the drug cartridge 112 and that a closed end portion 130 may be associated with both the distal end portion 126 and the proximal end portion 124 of the drug cartridge 112.

In an embodiment, the closed end portion may include a wall, surface or membrane that is able to be punctured with relative ease to open the fluid passageway of the drug cartridge. For example, as illustrated in FIG. 2, the wall 32 of the closed end portion 30 may be adapted to enable the wall to be punctured. In an embodiment, a closed end portion 30 associated with the proximal end 24 of the drug cartridge 12 is configured to include a surface configured to being punctured by a male connector of the port 44 of the pressure source 14 to establish fluid communication between the lumen of the male connector and the fluid passageway 22 of the drug cartridge 12.

FIG. 3 further illustrates an embodiment of the drug cartridge of the present disclosure having one or more retention barriers 140 and 142. The retention barriers 140 and 142 may include any substance or material that is configured to preventing the premature release of the predetermined amount of the drug 128 from the drug cartridge 112 until the drug 128 is exposed to the exertion pressure of the pressurized fluid released from the pressure source 14. Further, the substance of the retention barriers 140 and 142 is compatible with the drug in the drug cartridge and is pharmaceutically acceptable.

The substance of retention barriers 140 and 142 has a viscosity sufficient to prevent premature release of the predetermined amount of the drug 128 from the drug cartridge 112 until the drug is exposed to the pressurized fluid released from the pressure source 114. The viscosity of the retention barrier 140, for example, may be from about 4500 cP to about 5500 cP. In an embodiment, the viscosity of the retention barrier 140 is from about 4800 cP to about 5000 cP. Suitable substances to be used as a retention barrier 140 may include, but are not limited to, silicone-based oil such as MED-362 and other silicones and siloxanes having such viscosities. It should be appreciated that the greater the diameter of the inner wall 118 of the drug cartridge 112, the greater the viscosity required to retain the drug 122 and retention barriers 140 and 142 within the fluid passageway 122 of the drug cartridge 112.

The retention barriers 140 and 142 may include any suitable amount or volume of the substance. For example, in an embodiment, about 2 μl to about 20 μl of silicone oil is used as a retention barrier. In an embodiment, about 7.4 μl to about 13.3 μl silicone oil is used as a retention barrier. In an embodiment, each retention barrier includes about 10 μl silicone oil.

In an embodiment, a retention barrier 140 is positioned between the drug 128 and the opening of the proximal end 124 of the drug cartridge 112, and the retention barrier 142 is positioned within the fluid passageway 122 between the drug 128 and the opening of the distal end 126 of the drug cartridge 112. As illustrated in FIG. 3, one embodiment of the present disclosure includes both retention barriers 140, 142. It should be appreciated that the expulsion pressure for such an embodiment is the amount of pressure necessary to overcome the combined circumferential adhesive and frictional forces the retention barriers 140, 142 and the drug 128 exert along the surface of the inner wall 118 of the drug cartridge 112.

In an embodiment, the drug cartridge includes retention barrier 140 positioned between the drug 128 and the opening of the proximal end 124 of the drug cartridge 112 and retention barrier 142 positioned within the fluid passageway 122 between the drug 128 and the opening of the distal end 126 of the drug cartridge 112. The embodiment further includes closed end portion 130 associated with both proximal end portion 124 and distal end portion 126 of the drug cartridge 112.

Figure 4:
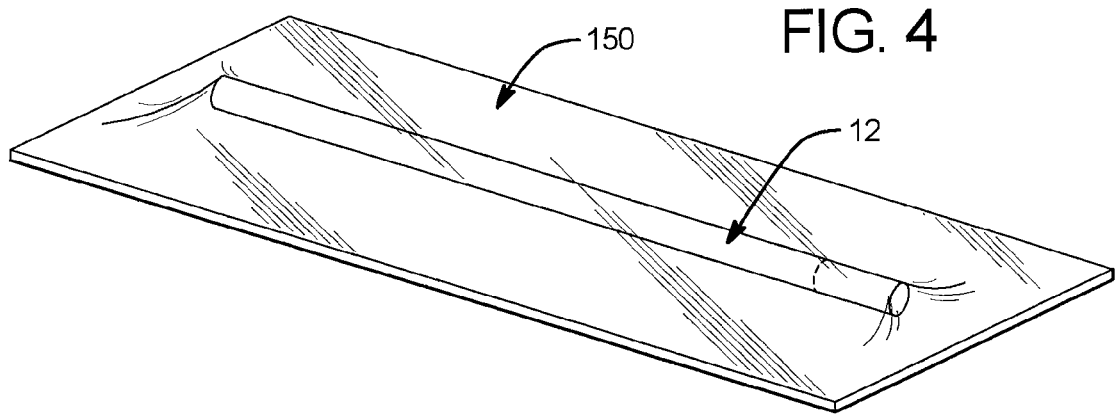
FIG. 4 is a perspective view of packaging of a drug cartridge according to an embodiment of the present disclosure.

Referring to FIG. 4, in an embodiment, at least one drug cartridge 12 is provided in packaging 150. The packaging 150 may include any suitable material such as paper, plastic, cellophane, foil or combinations thereof. The packaging 150 may include information describing the contents of the packaging 150 such as the name of the drug, drug dosage, drug concentration, drug volume, drug formulation, drug manufacturer, warnings, indications, administration instructions, intellectual property markings or any other suitable information. This information may be in the form of words on a label, a bar code, radio frequency identification label or any other suitable communication media or combinations thereof. Such information will enable a care giver to record exactly how much of the drug is administered to the patient. The packaging 150 may contain at least one drug cartridge 12.

In an embodiment, the pressure source 14 is provided in a kit with at least two individually packaged drug cartridges 12. The drug cartridges 12 may include the same or different drug, dosage of drug, concentration of drug, volume of drug, or formulation of drug. In an embodiment, each drug cartridge 12 included in a kit includes a unit dose of a drug. Alternatively, the predetermined amount of the drug 28 contained in each drug cartridge 12 is less than a unit dose of the drug such that the kit includes more than one drug cartridge 12 to be administered to administer a single unit dose of the drug.

For example, in an embodiment, a liquid unit dose spray kit for a topical anesthetic is provided. The kit includes one pressure source such as a propellant container and two cellophane-wrapped topical anesthetic drug cartridges. The propellant container includes an actuator release mechanism and contains compressed nitrogen gas. Each drug cartridge is in the form of a tube and contains about 0.15 mL of topical anesthetic in liquid form. A unit dose of the topical anesthetic is contained in the two tubes provided in the kit.

Figure 5:
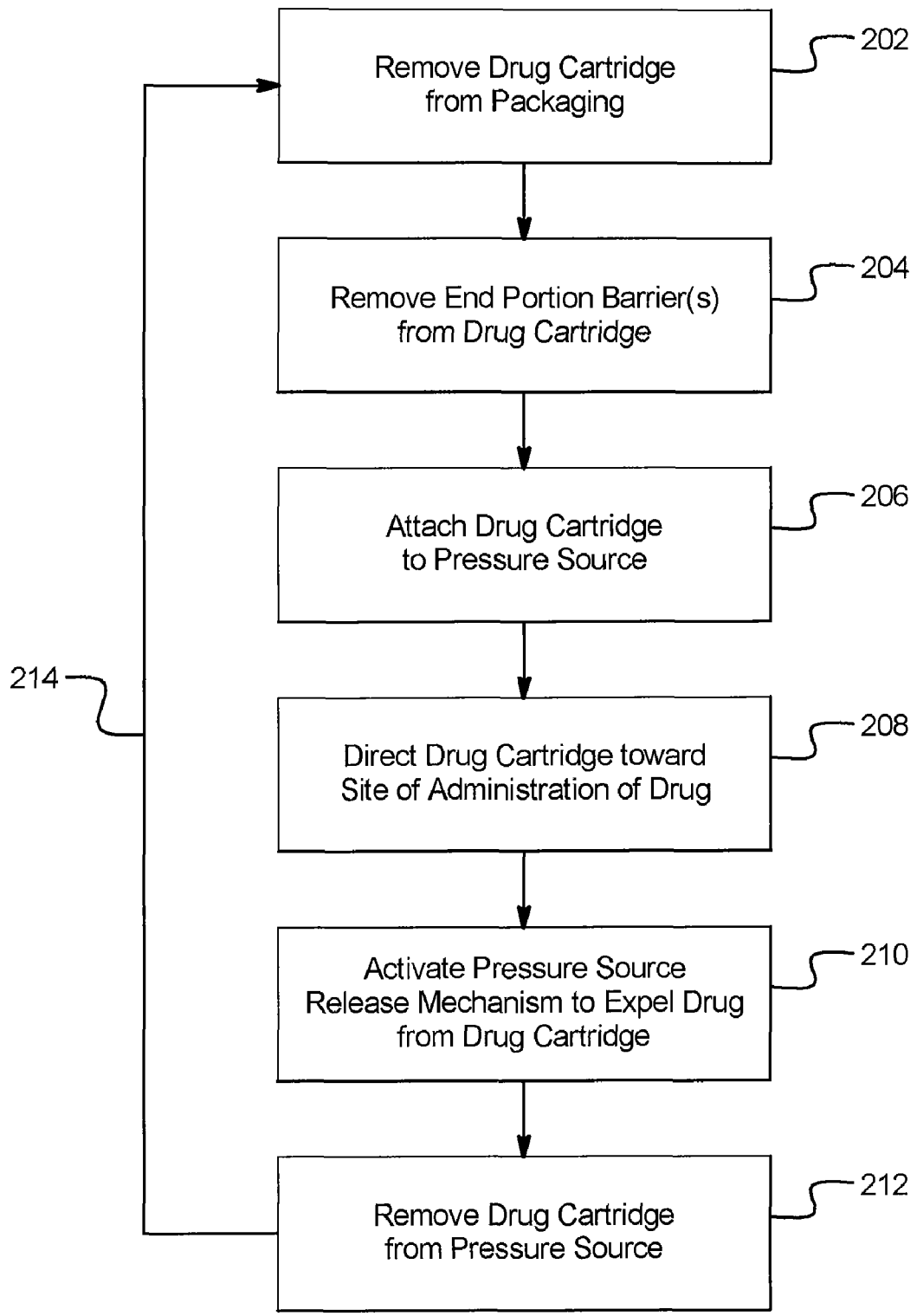
FIG. 5 is a diagram of steps of a method of drug delivery according to an embodiment of the present disclosure.

Referring to FIG. 5, the present disclosure includes methods of administering a plurality of predetermined doses of a drug. The method includes a providing a first drug cartridge containing a predetermined amount of the drug. The first drug cartridge is provided in packaging from which it is able to be removed 202. An end portion of the first drug cartridge (or an end portion barrier such as a cap) is able to be removed 204 to open the end portion of the first drug cartridge. The first drug cartridge is able to be attached to a pressure source to form a fluid connection between the first drug cartridge and the pressure source 206. The distal end of the first drug cartridge attached to the pressure source is then directed or oriented toward an area or site for administration of the drug 208. The release mechanism of the pressure source is able to be actuated or activated 210 to release sufficient pressurized fluid to generate an expulsion pressure to expel the predetermined amount of the drug from the first drug cartridge. The first drug cartridge may then be removed from the pressure source after the predetermined drug is discharged from the drug cartridge. The method further includes a step 214 of repeating steps 202, 204, 206, 208, 210 and 212 with a second drug cartridge containing a second predetermined amount of drug, a third drug cartridge containing a third predetermined amount of drug and so on. It should be appreciated that the steps described herein may be performed in any suitable sequence and may be repeated or not included in various embodiments of the present disclosure.

For example, referring to the liquid unit dose kit described above, a user may tear the cellophane packaging containing one of the tubular drug cartridges along a score line of the packaging and remove the drug cartridge from the packaging. The user may then firmly insert the end of the drug cartridge opposite the end having the weakened portion or score line into the actuator release button of the propellant container. The user then snaps off the end portion at the score line of the drug cartridge and removes the end portion completely from the drug cartridge.

In use, the user holds the end of the drug cartridge within a specified distance of the target site of administration, such as about one to two inches, from the site to be anesthetized. The actuator release mechanism on the propellant container is depressed to expel the topical anesthetic from the drug cartridge and the actuator release mechanism subsequently released. This process may be repeated with the second drug cartridge included in the kit.

In various embodiments, a kit may include multiple drug cartridges. The drug cartridges of the present disclosure may include or different colors, levels of transparencies, textures and combinations thereof, or be configured with different shapes, sizes and combinations thereof to differentiate between drugs or doses of drugs contained in the drug cartridges. For example, in an embodiment, a kit includes more than one type of drug. Each drug cartridge is colored to correspond with the color scheme established by the American Society for Testing and Materials for the drug contained within the drug cartridge. In an embodiment, the length of the drug cartridge containing an adult dose of a drug is greater than the length of a drug cartridge containing a pediatric dose of the same drug. In an embodiment, drug cartridges are shaped differently to attach to different pressure sources in a lock-and-key manner. For example, at least a portion of a first drug cartridge containing a first drug is shaped differently from a second drug cartridge containing a second drug such that only the first drug cartridge, and not the second drug cartridge, is able to form a fluid connection with a pressure source having a port with a shape complimentary to the first drug cartridge. It should be appreciated that a kit may include any suitable number of pressure sources having various amounts of pressurized fluid at various pressures and any suitable number of drug cartridges containing different drugs and doses of drugs.

In an embodiment, a drug cartridge filling device is provided. The filing device includes a filling cannula configured to be inserted into the fluid passageway of the drug cartridge to load the retention barriers and drug to be delivered from the drug cartridge by positive pressure injection, negative pressure, mechanical force, or any other suitable method of delivering the component to the drug cartridge. In an embodiment, the proximal end of the drug cartridge is frictionally fitted with an end portion in the form of a cap. The filling cannula is inserted to a level in the fluid passageway of the drug delivery device where 10 µl of silcone oil is infused through the filling cannula into the fluid passageway of the drug cartridge. The filling cannula is retracted distally to a level where 0.15 ml of the drug is infused through the filling cannula into the fluid passageway of the drug cartridge. The filling cannula is further retracted distally to a level where another 10 µl of silcone oil is infused through the filling cannula into the fluid passageway of the drug cartridge. The distal end of the drug cartridge is then frictionally fitted with an end cap. It should be appreciated that one or more drug filling devices may be used in any suitable manner to prepare a drug cartridge. It should be further appreciated that the steps described herein may be performed in any suitable sequence and may be repeated or not included in the preparation of a drug cartridge.

It should be understood that various changes and modifications to the presently preferred embodiments described herein will be apparent to those skilled in the art. Such changes and modifications can be made without departing from the spirit and scope of the present subject matter and without diminishing its intended advantages. For example, the embodiments of the present disclosure are not intended to be limited to delivery of a drug but can apply to the delivery of any substance from a container adapted to store a predetermined amount of the substance from which substantially all of the predetermined amount of the substance is delivered in response to an actuation of a pressure source. It is therefore intended that such changes and modifications be covered by the appended claims.

The invention is claimed as follows:

1. A drug delivery device comprising:
   a drug cartridge having a proximal end and a distal end, said drug cartridge defining a fluid passageway configured to contain a predetermined amount of a drug within said fluid passageway;
   a first retention barrier positioned within the fluid passageway of the drug cartridge between said drug and the proximal end of the drug cartridge;
   a second pharmaceutically acceptable retention barrier positioned within the fluid passageway of the drug cartridge between said drug and the distal end of the drug cartridge;
   a first closed end portion associated with the proximal end of the drug cartridge;
   a second closed end portion associated with the distal end of the drug cartridge; and
   a pressure source configured to removably couple to the proximal end of the drug cartridge to form a fluid connection with the fluid passageway of the drug cartridge, said connection configured to channel a pressurized fluid controllably released from the pressure source into the proximal end of the drug cartridge and through the fluid passageway of the drug cartridge toward the distal end of the drug cartridge to expel the predetermined amount of the drug and at least the second pharmaceutically acceptable retention barrier from the distal end of the drug cartridge.

2. The drug delivery device of claim 1, wherein the drug cartridge is in a substantially tubular form.

3. The drug delivery device of claim 1, wherein at least one of the first closed end portion and the second closed end portion is configured to be separated from the drug cartridge at a weakened portion of the drug cartridge.

4. The drug delivery device of claim 1, wherein at least one of the first closed end portion and the second closed end portion is in the form of a cap.

5. The drug delivery device of claim 1, wherein at least one of the first retention barrier and the second retention barrier includes a silicone oil.

6. The drug delivery device of claim 1, wherein the pressurized fluid is a gas.

7. The drug delivery device of claim 1, wherein the first retention Barrier is a pharmaceutically acceptable retention barrier.

* * * * *